US00PP29797P2

(12) United States Plant Patent
Los et al.

(10) Patent No.: US PP29,797 P2
(45) Date of Patent: Nov. 6, 2018

(54) ***MANDEVILLA* PLANT NAMED 'PATMANCR'**

(50) Latin Name: ***Mandevilla sanderi* (Hemsl.) Woodson**
Varietal Denomination: PATMANCR

(71) Applicant: Patio Plants V.O.F., Klazienaveen (NL)

(72) Inventors: Martijn Los, Klazienaveen (NL); Maurits van den Arend, Klazienaveen (NL)

(73) Assignee: Patio Plants V.O.F., Klazienaveen (NL)

( * ) Notice: Subject to any disclaimer, the term of this patent is extended or adjusted under 35 U.S.C. 154(b) by 0 days.

(21) Appl. No.: 15/731,797

(22) Filed: Aug. 2, 2017

(30) Foreign Application Priority Data

Jun. 2, 2017 (QZ) ..... PBR 2017/1474

(51) Int. Cl.
*A01H 5/02* (2018.01)

(52) U.S. Cl.
USPC ..... Plt./232

(58) Field of Classification Search
USPC ..... Plt./226, 232
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Mandevilla* cultivar named 'PATMANCR' which is characterized by a broad upright growth habit and broad obovate form, robust dark green foliage, an abundance of large pink flowers with a dark pink corolla tube, early flowering and a long flowering period, as well as the stability of these characteristics from generation to generation.

3 Drawing Sheets

Latin name of the genus and species: The Latin name of the genus and species of the novel variety disclosed herein is *Mandevilla sanderi* (Hemsl.) Woodson.

Variety denomination: The inventive variety of *Mandevilla* disclosed herein has been given the variety denomination 'PATMANCR'.

CROSS REFERENCE TO RELATED APPLICATIONS

This application claims priority to the Community Plant Variety Rights application number 2017/1474, filed Jun. 2, 2017, which is herein incorporated by reference.

BACKGROUND OF THE INVENTION

Parentage: 'PATMANCR' is the result of a planned breeding program. The new variety originated as a seedling from the crossing of an unnamed *Mandevilla sanderi* seedling developed and owned by the same inventors, the seed parent, with another unnamed *Mandevilla sanderi* seedling developed and owned by the same inventors, the pollen parent, in May of 2013. The crossing was made by the inventors at a greenhouse in Klazienaveen, The Netherlands. After observing the progeny of said cross, the new variety was selected in May of 2014 in Klazienaveen, The Netherlands.

Asexual Reproduction: Asexual reproduction of the new cultivar 'PATMANCR', by way of softwood stem cuttings, was first initiated in June of 2014 in Klazienaveen, The Netherlands. Through more than 3 subsequent generations, the unique features of this cultivar have proven to be stable and true to type.

SUMMARY OF THE INVENTION

The cultivar 'PATMANCR' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PATMANCR'. These characteristics in combination distinguish 'PATMANCR' as a new and distinct *Mandevilla* cultivar:

1. *Mandevilla* 'PATMANCR' exhibits a broad, upright growth habit and broad obovate form; and
2. *Mandevilla* 'PATMANCR' exhibits robust dark green foliage; and
3. *Mandevilla* 'PATMANCR' exhibits an abundance of large pink flowers with a dark pink corolla tube; and
4. *Mandevilla* 'PATMANCR' exhibits early flowering and a long flowering period.

BOTANICAL DESCRIPTION OF THE PLANT

Figure 1:
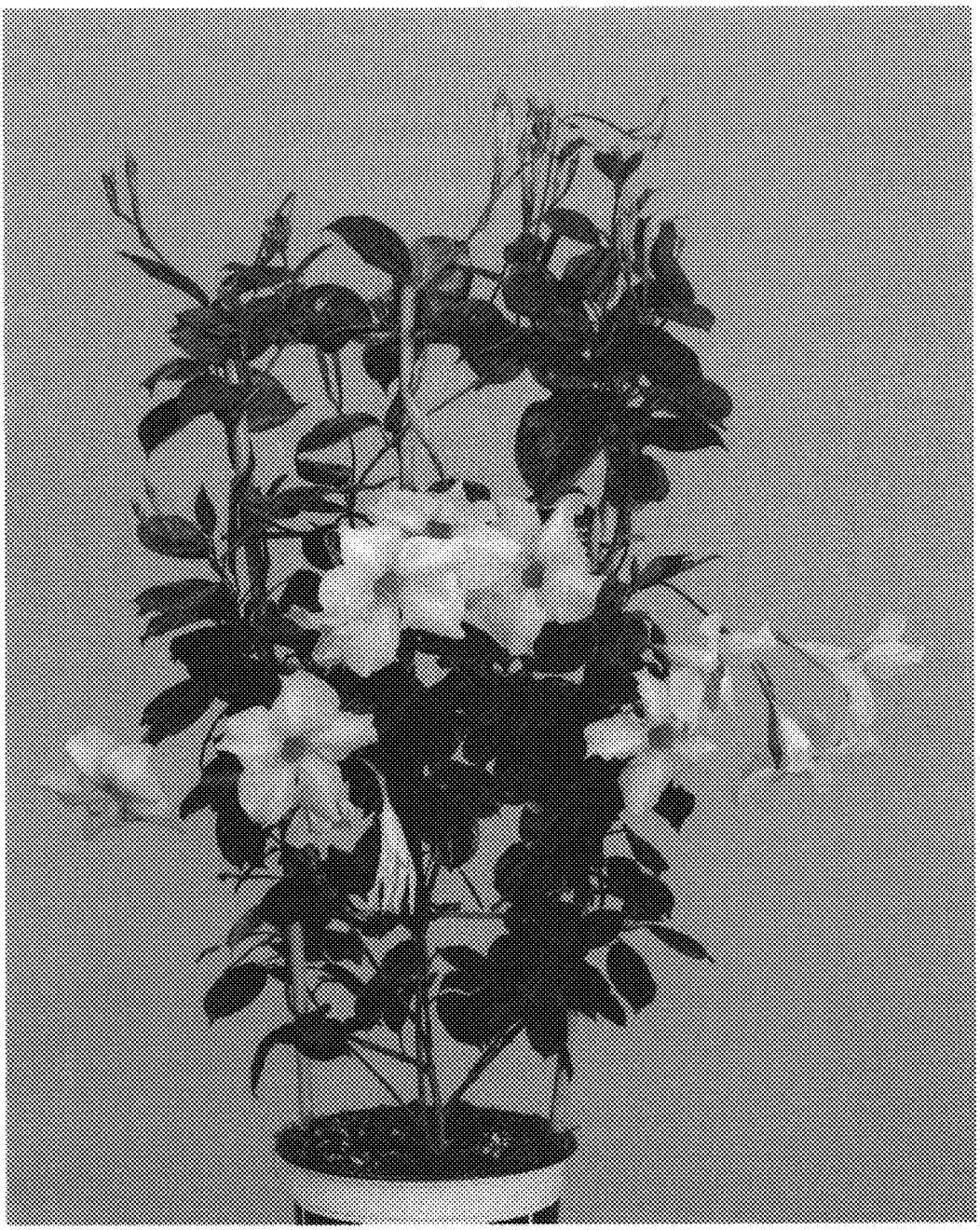
FIG. 1 illustrates, as nearly true as it is reasonably possible to make the same in color photographs of this type, an exemplary 8 month old 'PATMANCR' plant in a 19 cm nursery pot, grown in a greenhouse in Klazienaveen, The Netherlands.
Figure 2:
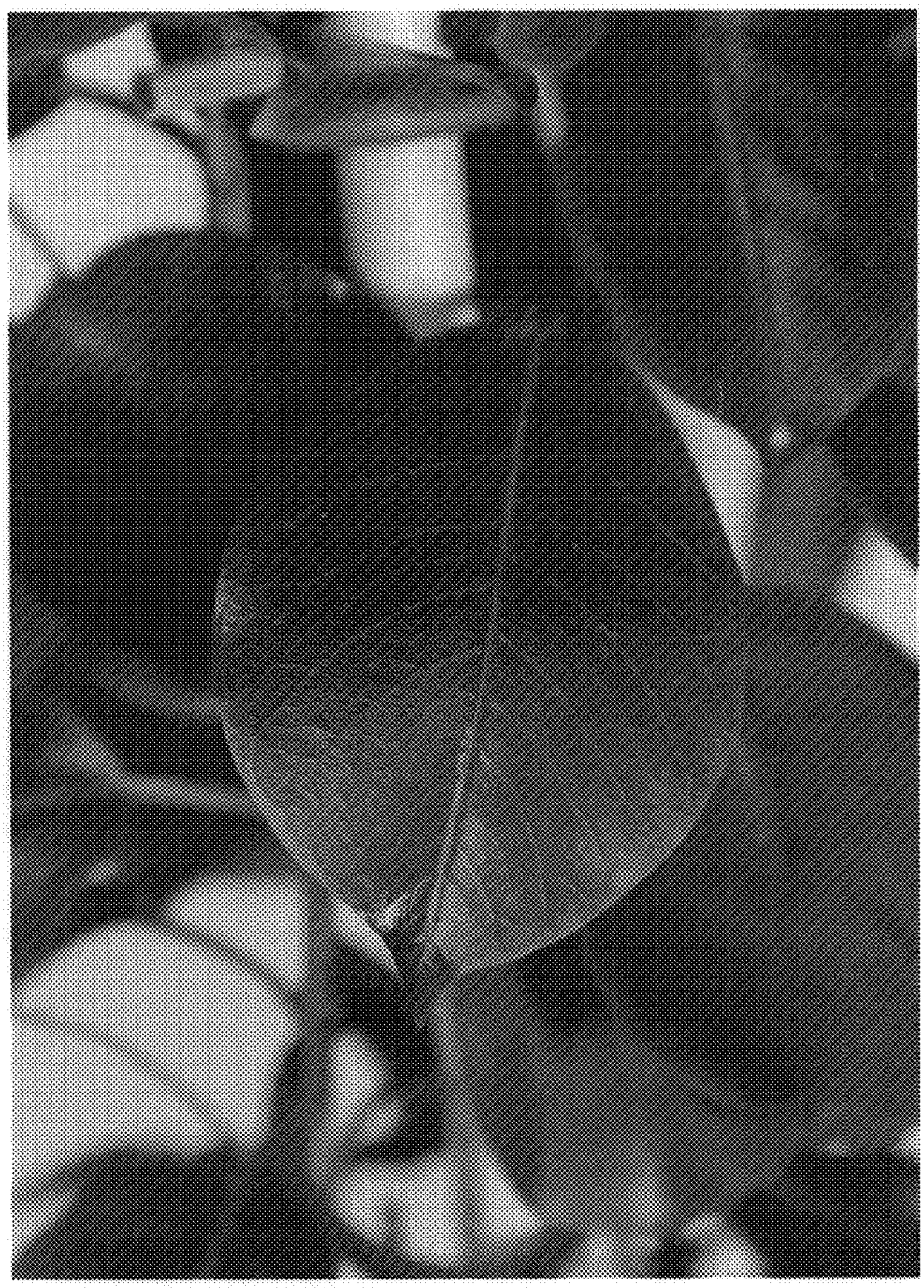
FIG. 2 illustrates, as nearly true as it is reasonably possible to make the same in color photographs of this type, the mature foliage of 'PATMANCR'.
Figure 3:
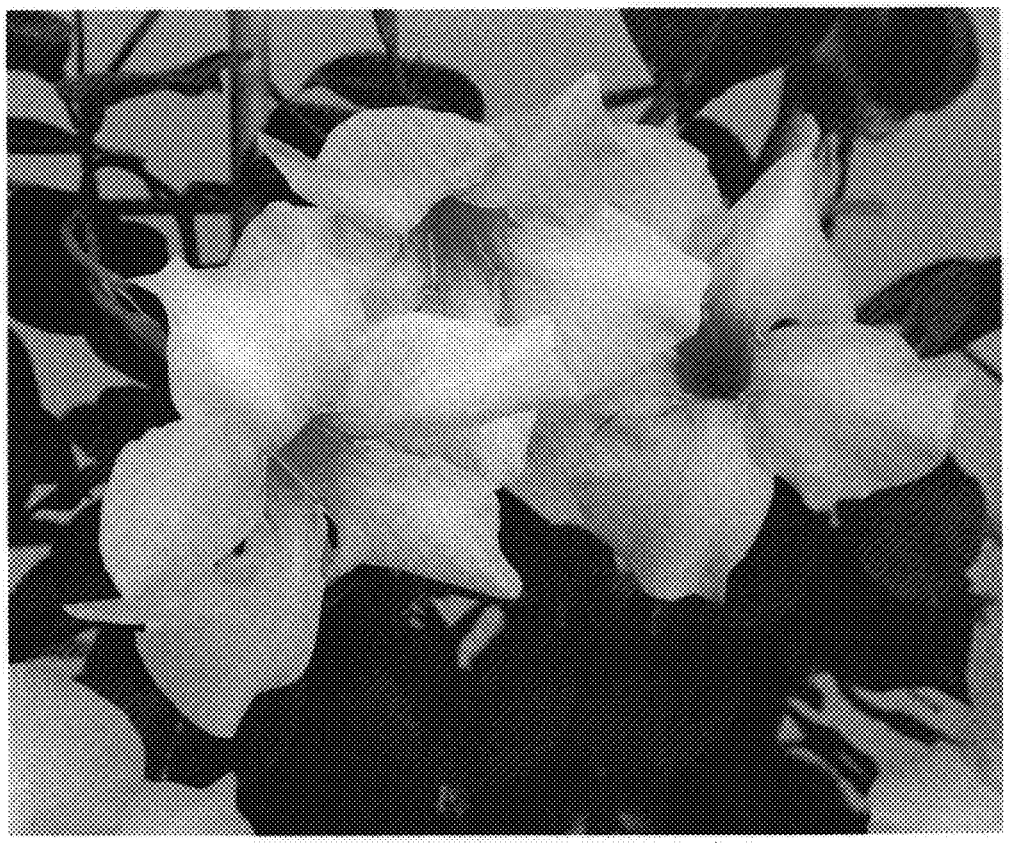
FIG. 3 illustrates, as nearly true as it is reasonably possible to make the same in color photographs of this type, an exemplary flower of 'PATMANCR'.

The following observations and measurements were made in April of 2017 and describe averages from a sample set of six specimens of 3 month old 'PATMANCR' plants grown in 17 cm nursery pots grown in a greenhouse in Klazienaveen, The Netherlands. Plants were produced using conventional greenhouse production protocols for *Mandevilla* which consisted of regular overhead and ebb and flood irrigation and fertigation applications. Pest or disease control measures were utilized in production as required. Plants were produced with full sun exposure and no photoperiodic treatments or artificial light was given to the plants.

Those skilled in the art will appreciate that certain characteristics will vary with older or, conversely, with younger plants. 'PATMANCR' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'PATMANCR' and comparisons with the parents and most similar commercial variety of *Mandevilla* are provided below.

Plant description:

*Growth habit*.—Vining perennial; broad upright.

*Plant shape*.—Obovate to broad obovate.

*Average height from base to top of foliage*.—67.2 cm.

*Average height from base to top of the floral plane*.—66.2 cm.

*Average width*.—53.1 cm.

*Growth rate*.—Moderate.

*Plant vigor*.—Moderate.

*Propagation method*.—Softwood stem cuttings; rooting is in initiated in approximately 10 to 14 days, with a fully rooted cutting in approximately 6 weeks, when grown in a greenhouse with an ambient average temperature of 25 degrees Celsius.

*Time to produce a finished plant*.—Approximately 45 weeks is required to produce a fully rooted and marketable 19 cm plant when grown under greenhouse conditions.

*Disease and pest resistance or susceptibility*.—Plants have not been observed to be susceptible or resistant to pathogens and pests common to *Mandeville sanderi*.

*Environmental tolerances*.—Adapt to at least USDA Zones 10 and 12, and temperatures ranging from at least 5 degrees to 40 degrees Celsius; moderate tolerance to rain; low to moderate tolerance to wind; low tolerance to drought.

Root system:

*General*.—Freely branching; moderately dense rooting.

*Texture*.—Fibrous.

*Color*.—Light brown.

Stem:

*Branching habit*.—Basally branching main stem; freely branching with lateral branches. Stems and branches exude a milky exudate when damaged.

*Number of main stems per plant*.—Four.

*Number of lateral branches per plant*.—Seven.

*Appearance; cross-section*.—Rounded.

*Length of lateral branches*.—45.9 cm.

*Diameter of lateral branches*.—0.35 cm at the widest point.

*Internode length on lateral branches*.—9.3 cm.

*Aspect*.—Upright; angle is approximately 27.5 degrees from vertical.

*Strength*.—Strong.

*Color, juvenile*.—Yellow-green, nearest to in between RHS 144A and 144B.

*Color, mature*.—Yellow-green, nearest to in between RHS 144B and 144C; surfaces exposed to sunlight are darker, in between 152A and 152B.

*Color at internodes*.—Yellow-green, nearest to in between RHS 144B and 144C; surfaces exposed to sunlight are darker, in between 152A and 152B.

*Texture and luster*.—Glabrous and moderately glossy.

*Color of bark on main stems*.—Greyed-brown, in between RHS 199A and 199B.

Foliage:

*Arrangement*.—Opposite.

*Division*.—Simple.

*Quantity*.—Average of 10 leaves per lateral branch.

*Lamina*.—Dimensions — 6.6 cm long and 4.4 cm wide, on average. Shape — Obovate or elliptic. Aspect — Flat to very slightly carinate. Apex — Short apiculate to abruptly acute. Base — Rounded to obtuse. Margin — Entire; not undulated. Pubescence, texture and luster of adaxial surface — Glabrous, smooth, and glossy. Pubescence, texture and luster of abaxial surface — Glabrous, smooth, and moderately glossy. Color — Juvenile foliage, adaxial surface — In between green, nearest to RHS NN137A, and yellow-green, nearest to RHS 147A; margins at the apex are greyed-red, in between RHS 178A and 178B. Juvenile foliage, abaxial surface — Yellow-green, in between RHS 148A and 152A; margins at the apex are greyed-red, in between RHS 178A and 178B. Mature foliage, adaxial surface — In between green, nearest to RHS NN137A, and yellow-green, nearest to RHS 147A, but darker. Mature foliage, abaxial surface — Yellow-green, in between RHS 146B and 147B. Venation — Pattern — Pinnate. Venation color, adaxial surface — Green, nearest to RHS 143A. Venation color, abaxial surface — Yellow-green, in between RHS 144B and 144C.

*Petiole*.—Length — 1.6 cm. Width — 0.175 cm. Texture — Smooth and glabrous. Luster — Moderately glossy. Strength — Moderately strong. Color, adaxial surface — Yellow-green, nearest to RHS 144A. Color, abaxial surface — Yellow-green, in between RHS 144B and 144C.

Inflorescence:

*Inflorescence arrangement*.—Axillary raceme bearing 2 to 6 flowers.

*Natural flowering season*.—Long flowering period; spring through autumn in USDA Hardiness Zones 10 through 12.

*Time to flower*.—Approximately 10 weeks from planting a rooted cutting.

*Dimensions*.—11.7 cm high and 13.2 cm in diameter.

*Quantity of flowers per inflorescence*.—3 on average; varying from 2 to 5.

*Quantity of flowers per plant*.—12.

*Quantity of flower buds per plant*.—56.

*Quantity of flowers and flower buds per plant*.—68.

*Peduncle*.—Dimensions — 7.4 cm long and 0.2 cm in diameter. Aspect — Upward and outward; at approximately 40 degrees to the lateral branch axis.

Strength — Medium. Texture and luster — Glabrous and moderately glossy. Color — Yellow-green, nearest to RHS 152A, on the upper surface, and greener underneath, nearest to RHS 144A.

Bud:

*Shape*.—Narrow oblanceolate.

*Dimensions*.—5.0 cm long and 0.9 cm in diameter.

*Pubescence, texture and luster*.—Glabrous, smooth and very slightly glossy.

*Color*.—The distal one-third portion of the bud is red, nearest to RHS 48A; the middle one-third section is yellow-green, in between RHS 145B and 145C; and, the proximal portion of the bud is yellow-green, nearest to RHS 145A.

Flower:

*Flowering habit*.—Moderately free flowering.

*Shape*.—Funnelform.

*Flower vertical height*.—7.3 cm.

*Flower diameter*.—9.6 cm.

*Diameter of floral throat*.—1.7 cm, at its widest point.

*Floral throat texture*.—Glabrous; smooth.

*Diameter of floral tube*.—1.9 cm at the distal end; at approximately one-third of the distance from the base, where tube begins to widen, the diameter is 0.5 cm.

*Length of floral tube*.—5.1 cm.

*Floral tube texture*.—Glabrous; smooth.

*Aspect*.—Flowers are outward facing.

*Fragrance*.—A faint pleasant fragrance; acidic-sweet.

*Lastingness*.—Approximately 10 days.

*Persistent*.—Self-cleaning.

*Pedicels*.—Dimensions — 2.7 cm long and 0.25 cm in diameter. Aspect — Upward and outward; approximately 20 degrees to the peduncle axis. Strength — Medium. Texture and luster — Glabrous, smooth, and moderately glossy. Color — Yellow-green, nearest to in between RHS 146C and 146D.

*Petals*.—Quantity of Petals — 5. Arrangement — Single whorl; petals imbricate and fused into an elongated tube at the base; lower 52.5 percent of the petals are fused. Shape of petal lobes — Spatulate. Dimensions, free portion of petals — 9.9 cm long and 4.3 cm wide. Apex — Unequal short apiculate. Base — Truncate; fused at the base. Margin — Entire; moderately to highly undulated. Aspect — Moderately reflexed. Pubescence, texture and luster of upper surface — Glabrous, velvety and very slightly glossy. Pubescence, texture and luster of lower surface — Glabrous, moderately velvety and very slightly glossy. Petal lobe color when opening, upper surface — Red-purple, nearest to RHS 62A, and fading lighter towards the floral tube, RHS 62C. Petal lobe color when opening, lower surface — Red-purple, nearest to RHS 62A, and fading lighter towards the floral tube, RHS 62C; central longitudinal band considerably lighter, nearest to RHS 69D. Petal lobe color when fully opened, upper surface — Red-purple, nearest to RHS 62A, and fading lighter towards the floral tube, RHS 69D. Petal lobe color when fully opened, lower surface — Red-purple, nearest to RHS 65A, and fading lighter towards the floral tube, RHS 65C; central longitudinal band considerably lighter, nearest to RHS 69D. Floral throat color — Red, nearest to RHS 55C. Floral throat venation color — Red, nearest to RHS 55B. Inner corolla tube color, when fully opened — Orange-red, RHS 33B; margins of the fused petals is yellow-orange, nearest to RHS 21B, and fading to white towards the throat, nearest to RHS NN155A. Outer corolla tube color, when fully opened — Red-purple, nearest to RHS 69B; lower proximal one-third portion of the tube is greyed-red, nearest to RHS 178C.

*Calyx*.—Shape — Rotate; single whorl of sepals. Dimensions — 0.6 cm in diameter and 0.5 cm tall. Sepals — Calyx dimensions — 0.55 cm in diameter and 0.6 cm tall. Arrangement — Sepals are free, rotate. Quantity — 5. Shape — Narrow triangular. Sepal dimensions — 0.5 cm long and 0.175 cm wide at the base. Apex — Narrow acuminate. Base — Cuneate. Margin — Entire; not undulated. Pubescence, texture and luster, upper surface — Smooth; glabrous; matte. Pubescence, texture and luster, lower surface — Smooth; glabrous; matte. Color when opening, upper surface — Yellow-green, nearest to RHS 146C, and suffused with greyed-red, nearest to RHS 179B; apex is greyed-red, nearest to RHS 179A. Color when opening, lower surface — Yellow-green, nearest to RHS 146C, and suffused with greyed-red, nearest to RHS 179B; apex is greyed-red, nearest to RHS 179A. Color when fully opened, upper surface — Yellow-green, nearest to in between RHS 144B and 144C; apex is greyed-red, nearest to RHS 179A. Color when fully opened, lower surface — Yellow-green, nearest to in between RHS 144B and 144C; apex is greyed-red, nearest to RHS 179A.

Reproductive organs:

*Androecium*.—Stamen quantity — 5. Attachment — Adnate. Filament length — 0.3 cm. Filament color — Yellow-green, nearest to RHS 151C. Anther attachment — Basifixed. Anther shape — Narrow sagitate. Anther length — 0.9 cm. Anther width — 0.125 cm. Anther color — Greyed-yellow, nearest to in between RHS 160A and 160B. Anther aspect — The five anthers are touching at their apices, thus forming a cone of anthers. Pollen, presence — Scarce. Pollen color — White, RHS 155A.

*Gynoecium*.—Pistil quantity — One. Pistil length — 2.1 cm. Style length — 1.9 cm. Style color — Yellow-green, nearest to RHS 145D. Stigma shape — Club-shaped. Stigma length — 0.2 cm. Stigma diameter — 0.2 cm. Stigma color — Yellow-green, nearest to RHS 145B; apex is darker, nearest to RHS 146D. Ovary color — Yellow-green, nearest to RHS 144A.

Seed and fruit: None observed.

COMPARISONS WITH THE PARENT PLANTS

Plants of the new cultivar 'PATMANCR' differ from the unnamed *Mandevilla sanderi* (Hemsl.) Woodson seed parent by the characteristics described in Table 1.

TABLE 1

| Characteristic | 'PATMANCR' | Unnamed seed parent |
|---|---|---|
| Leaf size. | Larger than the seed parent. | Smaller than 'PATMANCR'. |
| Flower size. | Larger than the seed parent. | Smaller than 'PATMANCR'. |

Plants of the new cultivar 'PATMANCR' differ from the unnamed *Mandevilla sanderi* (Hemsl.) Woodson pollen parent by the characteristics described in Table 2.

TABLE 2

| Characteristic | 'PATMANCR' | Unnamed pollen parent |
|---|---|---|
| Flowering season. | Longer than the pollen parent. | Shorter than 'PATMANCR' |
| Abundance of flowers at the apex of the plant. | More flowers than the pollen parent. | Less flowers than 'PATMANCR'. |
| General coloration of open flowers. | More vibrant pink. | Less vibrant pink. |

COMPARISON WITH THE MOST SIMILAR *MANDEVILLA* CULTIVAR KNOWN TO THE INVENTOR

Plants of the new cultivar 'PATMANCR' differ from the commercial variety, *Mandevilla* 'Sunparapibra' (U.S. Pat. No. 19,649), in the following characteristics described in Table 3 below.

TABLE 3

| Characteristic | 'PATMANCR' | 'Sunparapibra' |
|---|---|---|
| Leaf size. | Smaller than Sunparapibra'. | Larger than 'PATMANCR'. |
| Leaf color. | Darker green. | Lighter green. |
| Time to flower. | Earlier than 'Sunparapibra'. | Later than 'PATMANCR'. |
| Quantity of flowers. | More abundant than 'Sunparapibra'. | Less abundant than 'PATMANCR'. |
| Corolla aspect at anthesis. | More open than 'Sunparapibra'. | Less open than 'PATMANCR'. |
| Corolla diameter. | Larger than 'Sunparapibra'. | Smaller than 'PATMANCR'. |

That which is claimed is:

1. A new and distinct variety of *Mandevilla* plant named 'PATMANCR', substantially as described and illustrated herein.

* * * * *